United States Patent
Meune

(10) Patent No.: US 9,128,103 B2
(45) Date of Patent: Sep. 8, 2015

(54) MID-REGIONAL PRO-ATRIAL NATRIURETIC PEPTIDE (PRO-ANP) FOR THE IDENTIFICATION OF PATIENTS WITH ATRIAL FIBRILLATION WITH AN ONSET OF LESS THAN 48 HOURS AGO

(75) Inventor: Christophe Meune, Paris (FR)

(73) Assignee: B.R.A.H.M.S. GmbH, Hennigsdorf (DE)

( * ) Notice: Subject to any disclaimer, the term of this patent is extended or adjusted under 35 U.S.C. 154(b) by 0 days.

(21) Appl. No.: 14/235,561

(22) PCT Filed: Jul. 2, 2012

(86) PCT No.: PCT/EP2012/002778
§ 371 (c)(1),
(2), (4) Date: Jan. 28, 2014

(87) PCT Pub. No.: WO2013/013758
PCT Pub. Date: Jan. 31, 2013

(65) Prior Publication Data
US 2014/0170771 A1      Jun. 19, 2014

(30) Foreign Application Priority Data
Jul. 28, 2011 (EP) .................................... 11352009

(51) Int. Cl.
*G01N 33/53* (2006.01)
*G01N 33/68* (2006.01)

(52) U.S. Cl.
CPC ........ *G01N 33/6893* (2013.01); *G01N 33/6887* (2013.01); *G01N 2800/326* (2013.01)

(58) Field of Classification Search
None
See application file for complete search history.

(56) References Cited

PUBLICATIONS

Laukkanen et al. European Heart Journal 2006 vol. 27, p. 1230-1237.*
Latini et al. J. Internal Medicine 2010 vol. 269, p. 160-171.*
Smith et al. J. American College of Cardiology 2010 vol. 56, p. 1712-1719.*
Morgenthaler et al. Clinical Chem. 2004 vol. 50, p. 234-236.*
Palo et al. Clinical Chem. 2000 vol. 46, p. 843-847.*
International Searching Authority, International Search Report and Written Opinion in corresponding Application No. PCT/EP2012/002778, mailed Oct. 19, 2012 (11 pages).
Deftereos, S. et al., Short-Term Fluctuations of Plasma NT-proBNP Levels in Patients With New-Onset Atrial Fibrillation: A Way to Assess Time of Onset?, Heart, May 18, 2010, pp. 1033-1036, vol. 96, No. 13, Published by group.bmj.com.
Van Den Berg, Maarten P., et al., Depletion of Atrial Natriuretic Peptide During Longstanding Atrial Fibrillation, Europace, Sep. 1, 2004, pp. 433-437, vol. 6, No. 5, Elsevier Inc., U.S.
Meune, Christophe, et al., Mid-Regional Pro Atrial Natriuretic Peptide Allows the Accurate Identification of Patients With Atrial Fibrillation of Short Time of Onset: A Pilot Study, Clinical Biochemistry, Aug. 4, 2011, pp. 1315-1319, vol. 44, No. 16, Elsevier Inc., U.S.
The International Bureau of WIPO, International Preliminary Report on Patentability, International Application No. PCT/EP2012/002778, dated Jan. 28, 2014 (8 pages).

* cited by examiner

*Primary Examiner* — Jacob Cheu
(74) *Attorney, Agent, or Firm* — Wood, Herron & Evans, LLP

(57) ABSTRACT

The invention relates to a method for the determination of the time from onset of atrial fibrillation to presentation in a patient comprising the steps of: providing a sample of a bodily fluid of said patient, determining the level of proANP (SEQ ID NO: 1) or fragments thereof in said sample, correlating the level of proANP or fragments thereof to the time from the onset of atrial fibrillation to presentation of said patient, wherein said fragments have a length of at least 6 amino acid residues.

16 Claims, 2 Drawing Sheets

MID-REGIONAL PRO-ATRIAL NATRIURETIC PEPTIDE (PRO-ANP) FOR THE IDENTIFICATION OF PATIENTS WITH ATRIAL FIBRILLATION WITH AN ONSET OF LESS THAN 48 HOURS AGO

CROSS-REFERENCE TO RELATED APPLICATION

This application is a submission under 35 U.S.C. §371 of International Application No. PCT/EP2012/002778, filed Jul. 2, 2012, which claims priority to European Application No. 11352009.2, filed Jul. 28, 2011, the disclosures of which are hereby expressly incorporated by reference herein in their entireties.

FIELD OF THE INVENTION

The present invention is in the field of clinical diagnostics. Particularly, the present invention relates to the determination of the level of mid-regional pro-atrial natriuretic peptide (MR-proANP) in a sample derived from a bodily fluid of a patient with atrial fibrillation.

BACKGROUND OF THE INVENTION

Atrial Fibrillation (AF) is the most common cardiac arrhythmia that requires treatment and involves the two upper chambers (atria) of the heart. Approximately 2.2 million individuals in the United States and 4.5 million in the European Union have AF (Camm et al. 2010. *Eur Heart J.* 31:2369-2429; Go et al. 2001. *JAMA* 285:2370-2375). It also accounts for ⅓ of hospital admissions for cardiac rhythm disturbances (Fuster et al. 2006. *Circulation* 114:e257-354), and the rate of admissions for AF has risen in recent years (Fri berg et al. 2004. *Epidemiology* 14: 666-672). The prevalence of AF increases with age, from 0.5% at 40-50 years, to 5-15% at 80 years (Camm et al. 2010. *Eur Heart J.* 31:2369-2429). The incidence of atrial fibrillation also increases with age. In developed countries, the number of patients with atrial fibrillation is likely to increase during the next 50 years, due to the growing proportion of elderly individuals (Go et al. 2001. *JAMA* 285: 2370-2375).

Its name comes from the fibrillating (i.e., quivering) of the heart muscles of the atria, instead of a coordinated contraction. It can often be identified by taking a pulse and observing that the heartbeats do not occur at regular intervals. However, a stronger indicator of AF is the absence of P waves on an electrocardiogram (ECG or EKG), which are normally present when there is a coordinated atrial contraction at the beginning of each heart beat.

AF is associated with altered tolerance and increased risk of death, independently of other cardiac risk factors (Benjamin et al. 1998. *Circulation* 98: 946-952). The most prevalent and devastating consequence of AF is stroke. Strokes from AF account for 6-24% of all ischemic strokes (Narumiya et al. 2003. *Circulation Journal* 67 (1): 68-72). Electrical and pharmacological cardioversion of AF may be complicated of stroke following the restoration of an atrial mechanical activity (Camm et al. 2010. *Eur Heart J.* 31:2369-2429; Halperin et al. 1988. *Stroke* 19:937-941).

The American College of Cardiology (ACC), American Heart Association (AHA), and the European Society of Cardiology (ESC) recommend in their guidelines the following classification system based on simplicity and clinical relevance (Fuster et al. 2006. *Circulation* 114:e257-354). All atrial fibrillation patients are initially in the category called first detected AF. These patients may or may not have had previous undetected episodes. If a first detected episode self-terminates in less than 7 days and then another episode begins later on, the case has moved into the category of paroxysmal AF. Although patients in this category have episodes lasting up to 7 days, in most cases of paroxysmal AF the episodes will self-terminate in less than 24 hours. If instead the episode lasts for more than 7 days, it is unlikely to self-terminate (Levy 2000. *Curr Opin Cardiol* 15: 54-57) and it is called persistent AF. In this case, the episode may be terminated by cardioversion. If cardioversion is unsuccessful or it is not attempted, and the episode is ongoing for a long time (e.g. a year or more), the patient's AF is called permanent.

In addition to the above four AF categories, which are mainly defined by episode timing and termination, the ACC/AHA/ESC guidelines describe additional AF categories in terms of other characteristics of the patient (Fuster et al. 2006. *Circulation* 114:e257-354): Lone atrial fibrillation (LAF)— absence of clinical or echocardiographic findings of other cardiovascular disease (including hypertension), related pulmonary disease, or cardiac abnormalities such as enlargement of the left atrium, and age under 60 years; Nonvalvular AF—absence of rheumatic mitral valve disease, a prosthetic heart valve, or mitral valve repair; Secondary AF—occurs in the setting of a primary condition which may be the cause of the AF, such as acute myocardial infarction, cardiac surgery, pericarditis, myocarditis, hyperthyroidism, pulmonary embolism, pneumonia, or other acute pulmonary disease.

Atrial fibrillation is usually accompanied by symptoms related to a rapid heart rate. Rapid and irregular heart rates may be perceived as palpitations, exercise intolerance, and occasionally produce angina (if the rate is faster and puts the heart under strain) and congestive symptoms of shortness of breath or edema. Sometimes the arrhythmia will be identified only with the onset of a stroke or a transient ischemic attack (TIA). It is not uncommon for a patient to first become aware of AF from a routine physical examination or ECG, as it may be asymptomatic in many cases (Fuster et al. 2006. *Circulation* 114:e257-354).

As most cases of atrial fibrillation are secondary to other medical problems, the presence of chest pain or angina, symptoms of hyperthyroidism (an overactive thyroid gland) such as weight loss and diarrhea, and symptoms suggestive of lung disease would indicate an underlying cause. A previous history of stroke or TIA, as well as hypertension (high blood pressure), diabetes, heart failure and rheumatic fever, may indicate whether someone with AF is at a higher risk of complications (Fuster et al. 2006. *Circulation* 114:e257-354).

Atrial fibrillation may be treated with medications which either slow the heart rate or revert the heart rhythm back to normal. Cardioversion is a noninvasive conversion of an irregular heartbeat to a normal heartbeat using electrical or chemical means (Fuster et al. 2006. *Circulation* 114:e257-354). Surgical and catheter-based therapies may also be used to prevent recurrence of AF in certain individuals. People with AF are often given anticoagulants such as aspirin, heparin, warfarin or dabigatran to protect them from stroke.

The duration of AF becomes important when cardioversion is being considered, and it is generally accepted that patients who have an episode of AF of less than 48 hours may undergo prompt cardioversion safely whereas patients with an AF>48 hours have to be treated with anticoagulants for more than 3 weeks or to undergo transesophageal echocardiogram (TEE) prior to cardioversion (Camm et al. 2010. *Eur Heart J.* 31:2369-2429; Fuster et al. 2006. *Circulation* 114:e257-354; Page et al. 2004. *NEJM* 351:2408-2416; Klein et al. 2001. *NEJM* 344:1411-1420; Jessup et al. 2009. *Circulation* 119:

1977-2016). The duration of AF may be determined in patients who report acute palpitations, dyspnoea or syncope. However, asymptomatic or silent AF occurs frequently (Savelieva et al. 2000. *Pacing din Electrophysiol* 23:145-148): in the Canadian registry of AF, 21% of patients with newly diagnosed AF were asymptomatic (Kerr et al., 1996. *Eur Heart J* 17 Suppl C:48-51). In another study, 17% of patients had asymptomatic episodes of AF before they noted AF-related symptoms (Page et al. 2003. *Circulation* 107:1141-5). Overall, the clinical determination of the duration of AF, below or above 48 h, might be often hazardous in clinical practice pointing out the need for new tools to help clinicians in the accurate determination of AF duration prior to presentation.

Previous studies have suggested the possible merit of some biomarkers, mainly B-type natriuretic peptides, in the risk stratification of patients with AF or the prediction of AF occurrence (Defteros et at 2010. *Heart* 96:1033-1036; Jourdain et al. 2002. *Eur J Heart Fail* 4:263-267; Maisel et al. 2002. *NOM* 347:161-167; Thejus et al. 2009. *Indian Pacing Electrophysiol J* 9:1-4). Deftereos and collegues reported that patients with AF of less than 24 h and no heart failure have a particular pattern of NT-proBNP fluctuations that is characterized by a progressive rise within the first 24 h followed by rapid decline (Defteros et al. 2010. *Heart* 96:1033-1036). They concluded that obtaining two to three plasma NT-proBNP levels within 24 hours of presentation in patients with AF without heart failure, who cannot satisfactorily pinpoint the time of onset, may assist in determining whether the onset of the arrhythmia was recent, and that such information would be pertinent to decisions concerning anticoagulation and cardioversion. However, the triage of patients based on such NT-proBNP fluctuations may be hazardous in clinical practice and need prolonged monitoring of patients before a decision can be reached. In contrast, Tsuchida and Tanabe demonstrated that BNP was already elevated immediately within 4 hours after onset of AF and that the BNP level was not significantly correlated with the time elapsed after AF onset (Tsuchida and Tanabe 2004. *J Cardiol* 44:1-11).

SUMMARY OF THE INVENTION

Subject of the invention is a method for the determination of the time from onset of atrial fibrillation to presentation in a patient comprising the steps of:
i) providing a sample of a bodily fluid of said patient,
ii) determining the level of proANP or fragments thereof in said sample,
iii) correlating the level of proANP or fragments thereof to the time from the onset of atrial fibrillation to the presentation of said patient,
wherein said fragments have a length of at least 6 amino acid residues.

Preferred method variants are described in the dependent claims.

DETAILED DESCRIPTION OF THE INVENTION

Atrial fibrillation (AF) is defined as abnormal irregular heart rhythm with irregular generation of electrical signals in the atria of the heart that can be identified by taking a pulse and observing that the heartbeats do not occur at regular intervals and/or performing an electrocardiogram (ECG or EKG) where the absence of P waves, which are normally present when there is a coordinated atrial contraction at the beginning of each heart beat, is indicative of AF.

Cardioversion is a medical procedure by which an abnormally fast heart rate or cardiac arrhythmia is converted to a normal rhythm, using electricity or drugs (Shea et al. 2002. *Ciculation* 106:e176-178). Synchronized electrical cardioversion uses a therapeutic dose of electric current to the heart, at a specific moment in the cardiac cycle. Pharmacologic cardioversion, also called chemical cardioversion, uses antiarrhythmia medication instead of an electrical shock.

To perform synchronized electrical cardioversion two electrode pads are used (or, alternatively, the traditional hand-held "paddles"), each comprising a metallic plate which is faced with a saline based conductive gel. The pads are placed on the chest of the patient, or one is placed on the chest and one on the back. These are connected by cables to a machine which has the combined functions of an ECG display screen and the electrical function of a defibrillator. A synchronizing function (either manually operated or automatic) allows the cardioverter to deliver a reversion shock, by way of the pads, of a selected amount of electric current over a predefined number of milliseconds at the optimal moment in the cardiac cycle which corresponds to the R wave of the QRS complex on the ECG. Timing the shock to the R wave prevents the delivery of the shock during the vulnerable period (or relative refractory period) of the cardiac cycle, which could induce ventricular fibrillation. If the patient is conscious, various drugs are often used to help sedate the patient and make the procedure more tolerable. However, if the patient is hemodynamically unstable or unconscious, the shock is given immediately upon confirmation of the arrhythmia. When synchronized electrical cardioversion is performed as an elective procedure, the shocks can be performed in conjunction with drug therapy until sinus rhythm is attained. After the procedure, the patient is monitored to ensure stability of the sinus rhythm. Synchronized electrical cardioversion is used to treat hemodynamically significant supraventricular (or narrow complex) tachycardias, including atrial fibrillation and atrial flutter. It is also used in the emergent treatment of wide complex tachycardias, including ventricular tachycardia, when a pulse is present. Pulseless ventricular tachycardia and ventricular fibrillation are treated with unsynchronized shocks referred to as defibrillation. Electrical therapy is inappropriate for sinus tachycardia, which should always be a part of the differential diagnosis.

Various antiarrhythmic agents can be used to return the heart to normal sinus rhythm. Pharmacological cardioversion is an especially good option in patients with fibrillation of recent onset. Drugs that are effective at maintaining normal rhythm after electric cardioversion, can also be used for pharmacological cardioversion. Drugs like amiodarone, diltiazem, verapamil and metoprolol are frequently given before cardioversion to decrease the heart rate, stabilize the patient and increase the chance that card ioversion is successful. There are two classes of agents that are most effective for pharmacological cardioversion. Class I agents are sodium (Na) channel blockers (which slow conduction by blocking the $Na^+$ channel) and are divided into 3 subclasses a, b and c: Class Ia slows phase 0 depolarization in the ventricles and increases the absolute refractory period. Procainamide, quinidine and disopyramide are Class Ia agents. Class Ib drugs shorten phase 3 repolarization. They include lidocaine, mexiletine and phenyloin and finally class Ic drugs greatly slow phase 0 depolarization in the ventricles (however unlike 1a have no effect on the refractory period). Flecamide, moricizine and propafenone are Class Ic agents. Class II agents are beta blockers which inhibit SA and AV node depolarization and slow heart rate. They also decrease cardiac oxygen demand and can prevent cardiac remodeling. Not all beta blockers are the same, some are cardio selective (affecting only beta 1 receptors), others are non-selective (affecting beta 1 and 2 receptors). Beta blockers that target the beta-1 receptor are called cardio selective because beta-1 is responsible for increasing heart rate; hence a beta blocker will slow the heart rate. Class III agents prolong the repolarization by blocking outward K+ current. Amiodarone and sotalol are effective Class III agents. Ibutilide is another Class III agent but has a different mechanism of action (acts to promote influx of sodium through slow-sodium channels). It has been shown to be effective in acute cardioversion of recent-onset atrial fibrillation and atrial flutter. Class IV drugs are calcium (Ca) channel blockers. They work by inhibiting the action potential of the SA and AV nodes.

A transesophageal echocardiogram (TEE)-guided cardioversion strategy is recommended as an alternative to 3-week pre-cardioversion anticoagulation if experienced staff and appropriate facilities are available, and, when early cardioversion is needed, pre-cardioversion oral anticoagulant is not indicated due to patient choice or potential bleeding risks, or when there is a high risk of left atrial/left atrial appendage thrombus (Klein et al. 2001. NEJM 344:1411-1420). A TEE is an alternative way to perform an echocardiogram. A specialized probe containing an ultrasound transducer at its tip is passed into the patient's esophagus. This allows image and Doppler evaluation which can be recorded.

Increased risk of thrombo-embolism following cardioversion is well recognized. Therefore, anticoagulation is considered mandatory before elective cardioversion for AF of >48 h or AF of unknown duration. Thromboprophylaxis is recommended for electrical and pharmacological cardioversion of AF>48 h. In patients with a definite AF onset <48 h, cardioversion can be performed expediently under the cover of unfractionated heparin administered i.v. followed by infusion or subcutaneous low molecular weight heparin. In patients with risk factors for stroke (e.g. cardiac failure, hypertension, age, diabetes, previous stroke or TIA), oral anticoagulant therapy should be started after cardioversion and continued lifelong. No oral anticoagulant is required in patients without thrombo-embolic risk factors.

An anticoagulant is a substance that prevents coagulation; that is, it stops blood from clotting. A group of pharmaceuticals called anticoagulants can be used in vivo as a medication for thrombotic disorders. Oral anticoagulants include coumarins (vitamin K antagonists), e.g. warfarin acenocoumarol and phenprocoumon or phenindione. The anticoagulant heparin can be used by injection. Heparin and its low molecular weight derivatives (e.g. enoxaparin, dalteparin, tinzaparin) are effective at preventing deep vein thromboses and pulmonary embolism in patients at risk by preventing the formation of clots and extension of existing clots within the blood. Another type of anticoagulant is the direct thrombin inhibitor. Current members of this class include argatroban, lepirudin, bivalirudin, and dabigatran.

In one embodiment of the invention the time from onset of atrial fibrillation to presentation in a patient is determined to be above or below a certain time cut-off. In one preferred embodiment of the invention the time from onset of atrial fibrillation to presentation in a patient is determined to be 48 hours or above or below 48 hours. In another preferred embodiment of the invention the time from onset of atrial fibrillation to presentation in a patient is determined to be 24 hours or above or below 24 hours.

In a preferred embodiment of the invention, when the time from the onset of atrial fibrillation to presentation of said patient is determined to be below said time cut-off this is taken as an indicator that the patient should be applied to immediate cardioversion.

In another preferred embodiment of the invention, when the time from the onset of atrial fibrillation to presentation of said patient is determined to be at or above said time cut-off this is taken as an indicator that the patient should be treated with anticoagulants and/or should undergo transesophageal echocardiogram (TEE) prior to cardioversion.

In yet another preferred embodiment of the invention cardioversion preferably is electrical and/or pharmacological cardioversion.

Atrial natriuretic peptide (ANP), a member of the natriuretic peptide family, regulates several physiological parameters including diuresis and natriuresis, and lower arterial blood pressure (BP). It is predominantly produced in the atrium of the heart and comprises 98% of natriuretic peptides in the circulation (Vesely D L. Life 2002; 53:153-159). ANP is derived from the cleavage of its precursor pro-hormone, which is significantly more stable in the circulation than the mature peptide. A midregional fragment of the precursor hormone (amino acids 53-90 of NT-proANP), called midregional-proANP (MR-proANP), may be relatively resistant to degradation by exoproteases, unlike epitopes in the N- or C-terminals of proANP used in previous immunoassays (Morgenthaler N G et al. Clin Chem 2004; 50:234-236; Gerszten R E et al. 2008. Am J Physiol Lung Cell Mol Physiol).

In a preferred embodiment of the invention the level of proANP or fragments thereof is determined using at least one antibody directed against an amino acid sequence corresponding to the proANP fragment MR-proANP (SEQ ID NO: 4).

In a particular embodiment of the invention, additionally at least one clinical parameter is determined which may influence the level of proANP or fragments thereof in said patient. This clinical parameter is preferably selected from the group comprising age, gender, comorbidity and body mass index (BMI), most preferably from age and BMI. For example, the proANP level is known to increase with increasing age. This higher level should be taken into account when fixing cut-off values for older patients. Reference in connection with these clinical parameters can be made to Morgenthaler et al., Clin Chem. 2004, 234; Gegenhuber et al., Clin Chem. 2006, 827; Gegenhuber et al., J Card Fail. 2007, 42; von Haehling et al., J Am Coll Cardiol. 2007, 1973; Khaleghi et al., Am J. Cardiol. 2009, 1257; Krueger et al., Intensive Care Med. 2007, 2069; and Mueller et al., J Intern Med. 2006, 568, all incorporated herein by reference.

It is also possible and may improve the reliability of the results to determine one or more biomarkers in addition to proANP or fragments thereof, especially biomarkers related to atrial fibrillation or cardiovascular diseases in general. Preferred examples of such additional biomarkers are pro-BNP and fragments thereof, particularly NT-proBNP and/or BNP. Reference in this regard can be made to WO 2008/077396 A1 and WO 2008/106938 A2, which are incorporated herein by reference.

As mentioned herein, the term "fragment" refers to smaller proteins or peptides derivable from larger proteins or peptides, which hence comprise a partial sequence of the larger protein or peptide. Said fragments are derivable from the larger proteins or peptides by saponification of one or more of its peptide bonds. Said fragments are any fragments derivable from the prohormone of ANP (proANP; SEQ ID NO: 1). These fragments of proANP preferably relate to fragments of at least 6 amino acids in length, most preferably at least 12 amino acid residues in length. Known fragments of proANP include ANP (SEQ ID NO: 2), NT-proANP (SEQ ID NO: 3) and MR-proANP (SEQ ID NO: 4). Such fragments are preferably detectable with immunological assays as described herein.

As mentioned herein, an "assay" or "diagnostic assay" can be of any type applied in the field of diagnostics. Such an assay may be based on the binding of an analyte to be detected to one or more capture probes with a certain affinity. Concerning the interaction between capture molecules and target molecules or molecules of interest, the affinity constant is preferably greater than $10^8$ $M^{-1}$.

In the context of the present invention, "capture molecules" are molecules which may be used to bind target molecules or molecules of interest, i.e. analytes (i.e. in the context of the present invention the cardiovascular peptide(s)), from a sample. Capture molecules must thus be shaped adequately, both spatially and in terms of surface features, such as surface charge, hydrophobicity, hydrophilicity, presence or absence of Lewis donors and/or acceptors, to specifically bind the target molecules or molecules of interest. Hereby, the binding may for instance be mediated by ionic, van-der-Waals, pi-pi, sigma-pi, hydrophobic or hydrogen bond interactions or a combination of two or more of the aforementioned interactions between the capture molecules and the target molecules or molecules of interest. In the context of the present invention, capture molecules may for instance be selected from the group comprising a nucleic acid molecule, a carbohydrate molecule, a PNA molecule, a protein, an antibody, a peptide or a glycoprotein. Preferably, the capture molecules are antibodies, including fragments thereof with sufficient affinity to a target or molecule of interest, and including recombinant antibodies or recombinant anti-body fragments, as well as chemically and/or biochemically modified derivatives of said antibodies or fragments derived from the variant chain with a length of at least 12 amino acids thereof.

The preferred detection methods comprise immunoassays in various formats such as for instance radioimmunoassays (RIA), chemiluminescence- and fluorescence-immunoassays, Enzyme-linked immunoassays (ELISA), Luminex-based bead arrays, protein microarray assays, and rapid test formats, such as for instance immunochromatographic strip tests.

The assays can be homogenous or heterogeneous assays, competitive or non-competitive assays. In a particularly preferred embodiment, the assay is in the form of a sandwich assay, which is a non-competitive immunoassay, wherein the molecule to be detected and/or quantified is bound to a first antibody and to a second antibody. The first antibody may be bound to a solid phase, e.g. a bead, a surface of a well or other container, a chip or a strip, and the second anti-body is an antibody which is labeled, e.g. with a dye, with a radioisotope, or a reactive or catalytically active moiety. The amount of labeled antibody bound to the analyte is then measured by an appropriate method. The general composition and procedures involved with "sandwich assays" are well-established and known to the skilled person (*The Immunoassay Handbook*, Ed. David Wild, Elsevier LTD, Oxford; 3rd ed. (May 2005), ISBN-13: 978-0080445267; Hultschig C et al., *Curr Opin Chem. Biol.* 2006 February; 10(1):4-10. PMID: 16376134, incorporated herein by reference).

In a particularly preferred embodiment the assay comprises two capture molecules, preferably antibodies which are both present as dispersions in a liquid reaction mixture, wherein a first labeling component is attached to the first capture molecule, wherein said first labeling component is part of a labeling system based on fluorescence- or chemiluminescence-quenching or amplification, and a second labeling component of said marking system is attached to the second capture molecule, so that upon binding of both capture molecules to the analyte a measurable signal is generated that allows for the detection of the formed sandwich complexes in the solution comprising the sample.

Even more preferred, said labeling system comprises rare earth cryptates or rare earth chelates in combination with a fluorescence dye or chemiluminescence dye, in particular a dye of the cyanine type. In the context of the present invention, fluorescence based assays comprise the use of dyes, which may for instance be selected from the group comprising FAM (5- or 6-carboxyfluorescein), VIC, NED, fluorescein, fluoresceinisothiocyanate (FITC), IRD-700/800, cyanine dyes, auch as CY3, CY5, CY3.5, CY5.5, $Cy_7$, xanthene, 6-carboxy-2',4',7',4,7-hexachlorofluorescein (HEX), TET, 6-carboxy-4',5'-dichloro-2',7'-dimethoxy-fluorescein (JOE), N,N,N',N'-tetramethyl-6-carboxyrhodamine (TAMRA), 6-carboxy-X-rhodamine (ROX), 5-carboxyrhodamine-6G (R6G5), 6-carboxyrhodamine-6G (RG6), rhodamine, rhodamine green, rhodamine red, rhodamine 110, BODIPY dyes, such as BODIPY TMR, Oregon Green, coumarines, such as umbelliferone, benzimides, such as Hoechst 33258; phenanthridines, such as Texas Red, Yakima Yellow, Alexa Fluor, PET, ethidiumbromide, acridinium dyes, carbazol dyes, phenoxazine dyes, porphyrine dyes, polymethin dyes, and the like.

In the context of the present invention, chemiluminescence based assays comprise the use of dyes, based on the physical principles described for chemiluminescent materials in KirkOthmer, *Encyclopedia of chemical technology*, $4^{th}$ ed., executive editor, J. I. Kroschwitz; editor, M. Howe-Grant, John Wiley & Sons, 1993, vol. 15, p. 518-562, incorporated herein by reference, including citations on pages 551-562. Preferred chemiluminescent dyes are acridiniumesters.

Even more preferred, said labeling system comprises rare earth cryptates or rare earth chelates in combination with fluorescence dye.

The term "patient" as used herein refers to a living human or non-human organism that is receiving medical care or that should receive medical care due to a disease. This includes persons with no defined illness who are being investigated for signs of pathology.

The term "sample" as used herein refers to a sample of bodily fluid obtained for the purpose of diagnosis, prognosis, or evaluation of a subject of interest, such as a patient. Preferred test samples include blood, serum, plasma, cerebrospinal fluid, urine, saliva, sputum, and pleural effusions. In addition, one of skill in the art would realize that some test samples would be more readily analyzed following a fractionation or purification procedure, for example, separation of whole blood into serum or plasma components.

Thus, in a preferred embodiment of the invention the sample is selected from the group comprising a blood sample, a serum sample, a plasma sample, a cerebrospinal fluid sample, a saliva sample and a urine sample or an extract of any of the aforementioned samples. Preferably, the sample is a blood sample, most preferably a serum sample or a plasma sample.

Where appropriate, the sample may need to be homogenized, or extracted with a solvent prior to use in the present invention in order to obtain a liquid sample. A liquid sample hereby may be a solution or suspension. Liquid samples may be subjected to one or more pre-treatments prior to use in the present invention. Such pre-treatments include, but are not limited to dilution, filtration, centrifugation, concentration, sedimentation, precipitation, dialysis. Pre-treatments may also include the addition of chemical or biochemical substances to the solution, such as acids, bases, buffers, salts, solvents, reactive dyes, detergents, emulsifiers, chelators.

The sensitivity and specificity of a diagnostic and/or prognostic test depends on more than just the analytical "quality" of the test, they also depend on the definition of what constitutes an abnormal result. In practice, Receiver Operating Characteristic curves (ROC curves), are typically calculated by plotting the value of a variable versus its relative frequency in "normal" (i.e. apparently healthy) and "disease" populations (i.e. patients suffering from atrial fibrillation). For any particular marker, a distribution of marker levels for subjects with and without a disease will likely overlap. Under such conditions, a test does not absolutely distinguish normal from disease with 100% accuracy, and the area of overlap indicates where the test cannot distinguish normal from disease. A threshold is selected, above which (or below which, depending on how a marker changes with the disease) the test is considered to be abnormal and below which the test is considered to be normal. The area under the ROC curve is a measure of the probability that the perceived measurement will allow correct identification of a condition. ROC curves can be used even when test results do not necessarily give an accurate number. As long as one can rank results, one can create a ROC curve. For example, results of a test on "disease" samples might be ranked according to degree (e.g. 1=low, 2=normal, and 3=high). This ranking can be correlated to results in the "normal" population, and a ROC curve created. These methods are well known in the art (See, e.g., Hanley et al. 1982. *Radiology* 143: 29-36). Preferably, a ROC curve results in an area under the curve (AUC) of greater than about 0.5, more preferably greater than about 0.7, still more preferably greater than about 0.8, even more preferably greater than about 0.85, and most preferably greater than about 0.9. The term "about" in this context refers to +/−5% of a given measurement.

The horizontal axis of the ROC curve represents (1-specificity), which increases with the rate of false positives. The vertical axis of the curve represents sensitivity, which increases with the rate of true positives. Thus, for a particular cut-off selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

In certain embodiments, the marker or marker combination exhibits at least about 70% sensitivity, more preferably at least about 80% sensitivity, even more preferably at least about 85% sensitivity, still more preferably at least about 90% sensitivity, and most preferably at least about 95% sensitivity, combined with at least about 70% specificity, more preferably at least about 80% specificity, even more preferably at least about 85% specificity, still more preferably at least about 90% specificity, and most preferably at least about 95% specificity. In particularly preferred embodiments, both the sensitivity and specificity are at least about 75%, more preferably at least about 80%, even more preferably at least about 85%, still more preferably at least about 90%, and most preferably at least about 95%. The term "about" in this context refers to +/−5% of a given measurement.

Threshold levels can be obtained for instance from a Kaplan-Meier analysis, where the occurrence of a disease is correlated with the quartiles of the markers in the population. According to this analysis, subjects with marker levels above the 75th percentile have a significantly increased probability of belonging to the group having a time from the onset of atrial fibrillation to presentation of below a certain time cut-off. This result is further supported by Cox regression analysis with full adjustment for classical risk factors: The highest quartile versus all other subjects is highly significantly associated with the time interval below the certain time cut-off.

Other preferred cut-off values are for instance the 90th, 95th or 99th percentile of a normal population. By using a higher percentile than the 75th percentile, one reduces the number of false positive subjects identified, but one might miss to identify subjects, who are at moderate, albeit still increased risk. Thus, one might adopt the cut-off value depending on whether it is considered more appropriate to identify most of the subjects at risk at the expense of also identifying "false positives", or whether it is considered more appropriate to identify mainly the subjects at high risk at the expense of missing several subjects at moderate risk.

Other mathematical possibilities to calculate an individual's risk by using the individual's marker level value and other prognostic laboratory and clinical parameters are for instance the NR1 (Net Reclassification Index) or the IDI (Integrated Discrimination Index). The indices can be calculated according to Pencina (Pencina M J, et al.: *Evaluating the added predictive ability of a new marker: from area under the ROC curve to reclassification and beyond. Stat Med.* 2008; 27:157-172).

According to the method, the patient is diagnosed of having a time elapsed from the onset of atrial fibrillation to presentation of <48 h when said determined level of proANP or fragments thereof, especially the MR-proANP level, is lower than a predetermined threshold level. Preferably, the predetermined threshold level is between 100 and 350 pmol/L, more preferably between 100 pmol/L and 250 pmol/L, even more preferred between 100 pmol/L and 190 pmol/L, most preferred between 100 pmol/L and 160 pmol/L.

The above mentioned values might be different in other assays detecting proANP or fragments thereof, if these have been calibrated differently. The above mentioned values shall apply for such differently calibrated proANP assays accordingly, taking into account the differences in calibration. One possibility of quantifying the difference in calibration is a method comparison analysis (correlation) of the proANP assay in question with the MR-proANP assay used in the present invention by measuring proANP or fragments thereof in samples using both methods. Another possibility is to determine with the proANP assay in question, given this test has sufficient analytical sensitivity, the median proANP level of a representative normal population, compare results with the median analyte levels as described here and recalculate the calibration based on the difference obtained by this comparison.

DESCRIPTION OF DRAWINGS

The invention will now be described in more detail with reference to the attached drawings and the following examples. In the drawings

EXAMPLES

Study Design and Population

Figure 1:
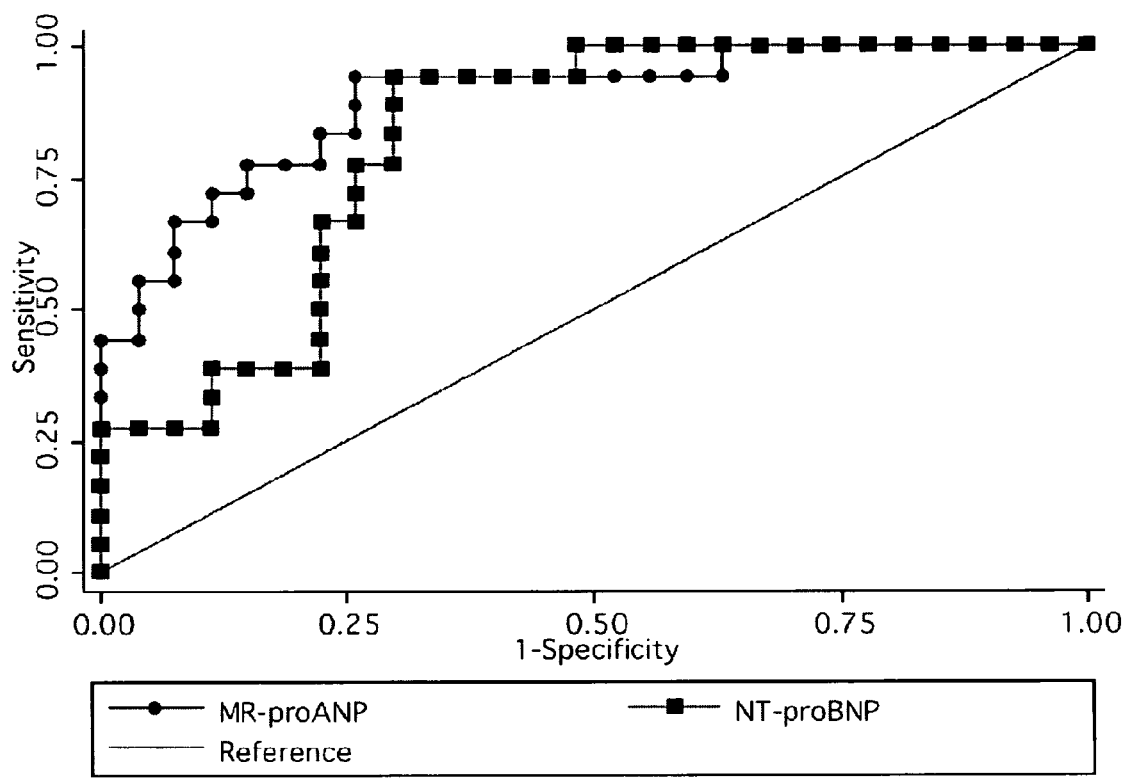
FIG. 1 shows a receiver operating curve for MR-proANP and NT-proBNP associated with time from the onset of atrial fibrillation to presentation of less than 48 hours.
Figure 2:
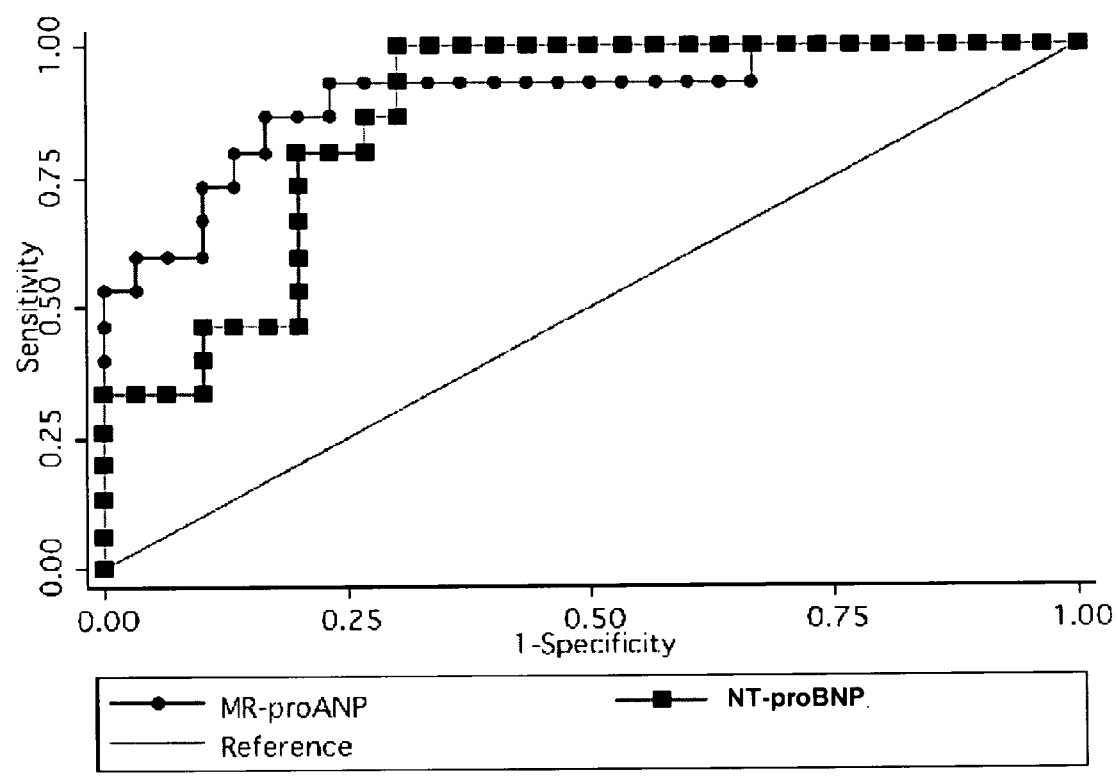
FIG. 2 shows a receiver operating curve for MR-proANP and NT-proBNP associated with time from the onset of atrial fibrillation to presentation of less than 24 hours.

From June 2010 to September 2010, consecutive patients who were referred to the department of cardiology of Cochin Hospital for the management of AF were considered for inclusion. AF was defined based on ECG as a cardiac arrhythmia with irregular RR interval (the time between two consecutive R waves in an electrocardiogram), no distinct P wave, and an atrial cycle length (when visible) variable and <200 ms. Exclusion criteria were 1) AF as a complication of an acute condition (i.e. acute myocardial infarction, following surgery, sepsis, acute respiratory failure), 2) patients with severe renal failure (creatinin clearance <30 ml/min), and 3) patients who presented with AF and concomitant acute decompensated heart failure clinically suspected on the basis of shortness of breath (new or worsening) and necessarily confirmed according to current guidelines (Jessup et al. 2009. *Circulation* 119:1977-2016). Patients gave written informed consent, and the local ethics committee approved the protocol.

Routine Clinical Assessment and Management

In addition to clinical history, physical examination, and 12-lead ECG, all patients underwent 1) chest radiography, 2) standard blood tests that included serologic tests of thyroid function and liver enzyme measurement, and 3) transthoracic echocardiography (TTE) performed by an experienced cardiologist using an ATL HDI 5000 system (ATL ultrasound and Bothell, Washington, D.C.) according to the guidelines of the American Society of Echocardiography.

The decision to perform TEE and the choice between a rhythm-control strategy with cardioversion or a rate-control strategy was left at the discretion of the physician. Patients for whom a cardioversion was considered had to be treated for at least 3 weeks with oral anticoagulant or to undergo TEE, according to current recommendations (Camm et al. 2010. *Eur Heart* 1. 31:2369-2429; Fuster et al. 2006. *Circulation* 114:e257-354).

Assessment of the Time of Onset to Presentation

AF was classified as paroxysmal, persistent or long-standing and the time of onset was independently determined by 2 cardiologists on the following items: 1) the onset of symptoms reported by the patient (mainly palpitations), 2) the possible previous in and out of-hospital ECGs and 24-holter monitoring results, and 3) the last cardiac rhythm noticed by out of hospital physicians in charge of the patients (including the general practitioner). Discrepancies were resolved by a third cardiologist.

Biochemical Analysis

Blood samples were collected in plastic tubes containing Li+-heparinate, and plasma was stored at −80° C. before analysis. Blood samples were collected at presentation, in a patient in a supine position for at least 30 min, from a peripheral antecubital vein. MR-proANP was measured using the Kryptor analyzer (B.R.A.H.M.S GmbH, Hennigsdorf, Germany). This fluoroimmunoassay uses the Time Resolved Amplified Cryptate Emission (TRACE) technology, which is based on a non-radioactive energy transfer from a donor molecule (cryptate) to an acceptor molecule (XL665) as a result of a completed immune reaction. The analytical performances of the method have been evaluated and described elsewhere. In our laboratory, coefficients of variation (CV) were found to be <5%:3.4% at 419.0 pmol/L and 3.7% at 89.2 pmol/L (Chenevier-Gobeaux et al. 2010. *Clin Chem* 56:1708-1717).

Plasma NT-proBNP levels were measured using a commercially available immunofluorescent assay (Elecsys proBNP, Roche Diagnostics, Mannheim, Germany). The assay has a functional sensitivity of 30 pg/ml, with an upper measuring limit of 35000 pg/ml and a coefficient of variation in the range of 1.0-6.0%.

Statistical Analysis

Values are expressed as means±standard deviation, medians with interquartile [IQR] range, or counts and percentages as appropriate. The existence of any correlation between the natriuretic peptides and other variable was investigated using Spearman correlation. The capacity of natriuretic peptides and other clinical and laboratory parameters to discriminate between patients with recent onset (<48 h) from patients with more prolonged AF was first investigated in univariate analysis using Student t-test or Mann-Whitney U test for continuous variables and chisquare or Fisher exact test for difference in frequencies, as appropriate. Multivariate logistic regression was then performed, including all variables that emerged from univariate analysis, to test the possible independent diagnostic information offered by natriuretic peptides. Receiver operator characteristic (ROC) curves were constructed to assess the sensitivity and specificity throughout the concentrations of natriuretic peptides; the ideal cut-off value was determined from the ROC curve and sensitivity and specificity are reported. All statistical analyses were performed using STATA Version 10.1 (StataCorp LP, College Station, Tex.) and a p-value of less than 0.05 was considered statistically significant.

Results

From June 2010 to September 2010, 57 patients were referred for the management of AF. Of these, 9 patients could not be included (4 patients had acute myocardial infarction, 3 had cardiogenic or non-cardiogenic shock, 1 had severe renal failure and 1 had acute decompensated heart failure). Natriuretic peptides were not measured in one additional patient. Therefore 47 patients were included. Patients' characteristics for a time of onset of AF to presentation of </≥48 h are listed in Table 1. Median age at inclusion was 72 years [61-81] and the sex ratio was 1.9. AF was paroxysmal in 22 patients, persistent in 6 and long-lasting in 19. Nineteen patients (40.4%) had an AF onset within 48 h; median duration of AF was 5 days [1-120] in the whole cohort.

MR-proANP levels ranged from 78.8 to 903.3 pmol/L. MR-proANP correlated partially but significantly with time from onset of AF to presentation, LV ejection fraction (LVEF), haemoglobin, but not heart rate or creatinin concentration (Table 2). Moreover, MR-proANP and NT-proBNP were significantly correlated (Spearman r=0.71, p<0.001). The MR-proANP concentrations among the different subgroups (paroxysmal, persistent and longstanding AF, respectively) are represented Table 3.

Analysis Time from Onset of AF to Presentation (</≥48 h)

Patients with an AF onset <48 h had markedly decreased MR-proANP versus patients with an AF onset ≥48 h (144.0 [129.2-213.7] pmol/L versus 321.7 [236.4-425.6] pmol/L respectively, p<0.001) (Table 3). Other variables associated with AF<48 h were lower age, increased heart rate, preserved LVEF (left ventricular ejection fraction), preserved haemoglobin (Table 1). In multivariate analysis, MR-proANP was the only variable that remained associated with AF of less than 48 h (p=0.021).

The area under the ROC curve to identify patients with AF onset of less than 48 hours prior to admission was 0.90 for MR-proANP and 0.82 for NT-proBNP, respectively (p<0.05; FIG. 1). The removal of patients with LVEF<50% (12 patients) did not alter the results; in this case MR-proANP was 140.8 [129.2-191.6] pmol/L in patients with AF<48 h versus 321.7 [213.5-422.0] pmol/L in patients with AF ≥48 h (p<0.001).

Based on the ROC curve analysis, we identified two possible cut-off values for MR-proANP to detect patients with AF onset of less than 48 hours prior to admission. A cut-off value of 191.6 pmol/L would result in a sensitivity and specificity of 85.7% and 73.8%, respectively; a cut-off value of 161.9 pmol/L would result in a sensitivity of 92.9% and a specificity of 63.2%. The sensitivities and specificities of exemplary MR-proANP cut-off values to differentiate between patients with a time from onset of AF to presentation of <48 h from patients with a time from onset of AF to presentation of ≥48 h are given in table 4.

SEQUENCES
SEQ ID NO: 1
(amino acid sequence of proANP):
1 NPMYNAVSNA DLMDFKNLLD HLEEKMPLED EVVPPQVLSE
PNEEAGAALS
51 PLPEVPPWTG EVSPAQRDGG ALGRGPWDSS DRSALLKSKL
RALLTAPRSL
101 RRSSCFGGRM DRIGAQSGLG CNSFRY SEQ ID NO: 2
(amino acid sequence of ANP):
1 SLRRSSCFGG RMDRIGAQSG LGCNSFRY SEQ ID NO: 3
(amino acid sequence of NT-proANP):
1 NPMYNAVSNA DLMDFKNLLD HLEEKMPLED EVVPPQVLSE
PNEEAGAALS
51 PLPEVPPWTG EVSPAQRDGG ALGRGPWDSS DRSALLKSKL
RALLTAPR SEQ ID NO: 4
(amino acid sequence of MR-proANP):
1 PEVPPWTGEV SPAQRDGGAL GRGPWDSSDR SALLKSKL SEQ ID NO: 5
(amino acid sequence of pro-BNP):
1 HPLGSPGSAS DLETSGLQEQ RNHLQGKLSE LQVEQTSLEP
LQESPRPTGV
51 WKSREVATEG IRGHRKMVLY TLRAPRSPKM VQGSGCFGRK
MDRISSSSGL
101 GCKVLRRH SEQ ID NO: 6
(amino acid sequence of BNP):
1 SPKMVQGSGC FGRKMDRISS SSGLGCKVLR RH SEQ ID NO: 7
(amino acid sequence of NT-pro-BNP):
1 HPLGSPGSAS DLETSGLQEQ RNHLQGKLSE LQVEQTSLEP
LQESPRPTGV
51 WKSREVATEG IRGHRKMVLY TLRAPR

TABLE 1

Patients characteristics (time from onset of AF to presentation </≥48 h)

|  | AF < 48 h (n = 19) | AF ≥ 48 h (n = 28) | p |
|---|---|---|---|
| Age, year | 66 [46-74] | 75 [66-83] | 0.010 |
| Male sex | 14 (74) | 17 (61) | 0.357 |
| Hypertension | 7 (37) | 17 (61) | 0.108 |
| Hypercholesterolemia | 5 (26) | 9 (32) | 0.668 |
| Diabetes | 3 (16) | 7 (25) | 0.449 |
| Obesity | 8 (42) | 10 (36) | 0.658 |
| Smoking | 4 (21) | 3 (11) | 0.329 |
| Previous AMI | 2 (11) | 1 (4) | 0.338 |
| Previous AF | 4 (36) | 16 (57) | 0.243 |
| Chest pain | 2 (11) | 1 (4) | 0.338 |
| Dyspnoea | 4 (21) | 10 (36) | 0.281 |
| Lipothymia | 7 (37) | 3 (11) | 0.067 |
| Heart rate, bpm | 135 ± 31 | 101 ± 25 | <0.001 |
| Systolic BP, mmHg | 134 ± 13 | 128 ± 19 | 0.310 |
| Diastolic BP, mmHg | 74 ± 10 | 69 ± 11 | 0.102 |
| Creatinin, μmol/L | 87 ± 21 | 97 ± 31 | 0.244 |
| Haemoglobin, g/dL | 15.0 ± 2.1 | 12.9 ± 2.0 | 0.002 |
| Increased cTn concentration | 1 (5) | 2 (7) | 0.645 |
| Echocardiography | | | |
| LV end-diastolic diameter, mm | 49 ± 7 | 52 ± 9 | 0.320 |
| Septal thickness, mm | 11 ± 1 | 12 ± 2 | 0.422 |
| LVEF, % | 59 ± 9 | 48 ± 16 | 0.048 |
| Significant valvular disease[+] | 2 (20) | 11 (46) | 0.158 |
| Pulmonary arterial pressure, mmHg | 39 ± 5 | 41 ± 11 | 0.366 |
| Left atria surface, mm$^2$ | 18 ± 5 | 39 ± 36 | 0.153 |

AMI: acute myocardial infarction
AF: atrial fibrillation
cTn: cardiac troponin
LV: left ventricular
LVEF: left ventricular ejection fraction
Significant valvular disease is defined as valve stenosis and/or mild valve regurgitation

TABLE 2

Possible correlation between MR-proANP concentration and selected variables

| Variable | Spearman's Rho | p |
|---|---|---|
| Atrial fibrillation duration (days) | 0.60 | <0.001 |
| Heart rate | −0.26 | 0.077 |
| Haemoglobin (g/dL) | −0.47 | 0.001 |
| Creatinin concentration (μmol/L) | 0.17 | 0.268 |
| Left ventricular ejection fraction | −0.40 | 0.019 |
| Pulmonary systolic arterial pressure | 0.39 | 0.061 |

TABLE 3

MR-proANP plasma concentrations according to AF classification and time from onset to presentation

| VARIABLE | MR-proANP (pmol/L) | p |
|---|---|---|
| Time from onset of AF to presentation: | | |
| <48 h | 144.0 [129.2-213.7] | <0.001 |
| ≥4≥ h | 321.7 [236.4-425.6] | |
| Time from onset of AF to presentation: | | |
| <24 h | 111.5 [86.0-178.9] | <0.001 |
| ≥2≥ h | 290.4 [218.6-422.0] | |
| AF classification: | | |
| Paroxysmal | 157.8 [133.4-241.7] | <0.001 |
| Persistent | 380.2 [349.5-490.9] | |
| Long-standing | 275.7 [197.9-429.1] | |

TABLE 4

Specificity and sensitivity values at different cut-off levels for MR-proANP to differentiate patients with a time from onset of AF to presentation of <48 h from patients with a time from onset of AF to presentation of ≥48 h)

| MR-proANP cut-off value (pmol/L) | Specificity (in %) | Sensitivity (in %) |
|---|---|---|
| 93.8 | 15.8 | 100.0 |
| 129.2 | 21.1 | 100.0 |
| 144.0 | 47.4 | 96.4 |
| 161.9 | 63.2 | 92.9 |
| 168.1 | 68.4 | 89.3 |
| 191.6 | 73.8 | 85.7 |

TABLE 4-continued

Specificity and sensitivity values at different cut-off levels for MR-proANP to differentiate patients with a time from onset of AF to presentation of <48 h from patients with a time from onset of AF to presentation of ≥48 h)

| MR-proANP cut-off value (pmol/L) | Specificity (in %) | Sensitivity (in %) |
|---|---|---|
| 218.6 | 79.0 | 78.6 |
| 254.1 | 89.5 | 75.0 |
| 336.9 | 94.7 | 50.0 |
| 402.6 | 100.0 | 35.7 |

The invention claimed is:

1. A method for the determination of the time from onset of atrial fibrillation to presentation of a patient comprising the steps of:
   (i) providing a sample of a bodily fluid of said patient,
   (ii) determining the level of proANP fragment MR-proANP (SEQ ID No: 4) in said sample,
   (iii) correlating the level of proANP fragment MR-proANP (SEQ ID No: 4) to the time from the onset of atrial fibrillation to presentation of said patient, and
   (iv) determining whether the time from the onset of atrial fibrillation to presentation of the patient is at or above a time cut-off value or below said time cut-off value, wherein said time cut-off value is chosen from 48 hours and 24 hours.

2. The method according to claim 1, wherein the time cut-off value is 48 hours.

3. The method according to claim 1, wherein the time cut-off value is 24 hours.

4. The method according to claim 1, wherein said sample is selected from blood, serum, plasma, cerebrospinal fluid, urine or saliva.

5. The method according to claim 1, wherein the level of proANP or fragments thereof is determined using at least one antibody directed against an amino acid sequence corresponding to the proANP fragment MR-proANP (SEQ ID NO: 4).

6. The method according to claim 1, wherein, when the time from the onset of atrial fibrillation to presentation of said patient is determined to be below said time cut-off value, this is taken as an indicator that the patient should be applied to immediate cardioversion.

7. The method according to claim 1, wherein, when the time from the onset of atrial fibrillation to presentation of said patient is determined to be at or above said time cut-off value, this is taken as an indicator that the patient should be treated with anticoagulants and/or should undergo transesophageal echocardiogram (TEE) prior to cardioversion.

8. The method according to claim 6, wherein cardioversion is electrical and/or pharmacological cardioversion.

9. The method according to claim 1, wherein the time from the onset of atrial fibrillation to presentation of the patient is determined to be below said time cut-off value when said determined level of proANP fragment MR-proANP (SEQ ID No: 4) is lower than a predetermined threshold level.

10. The method according to claim 9, wherein the predetermined threshold level is between 100 and 350 pmol/L.

11. The method according to claim 1, wherein at least one biomarker is determined in addition to proANP fragment MR-proANP (SEQ ID No: 4), wherein the at least one biomarker is chosen from a biomarker related to a cardiovascular disease, a biomarker related to atrial fibrillation, pro-BNP and fragments thereof, NT-proBNP, BNP, and combinations thereof.

12. The method according to claim 1, wherein additionally at least one clinical parameter is determined which may influence the level of proANP or fragments thereof in said patient.

13. The method according to claim 12, wherein the clinical parameter is chosen from age, gender, comorbidity and body mass index (BMI).

14. The method according to claim 9, wherein the predetermined threshold level is between 100 pmol/L and 250 pmol/L.

15. The method according to claim 9, wherein the predetermined threshold level is between 100 pmol/L and 190 pmol/L.

16. The method according to claim 9, wherein the predetermined threshold level is between 100 pmol/L and 160 pmol/L.

* * * * *

SEQUENCE LISTING

<160> NUMBER OF SEQ ID NOS: 7

<210> SEQ ID NO 1
<211> LENGTH: 126
<212> TYPE: PRT
<213> ORGANISM: Homo sapiens

<400> SEQUENCE: 1

```
Asn Pro Met Tyr Asn Ala Val Ser Asn Ala Asp Leu Met Asp Phe Lys
1               5                   10                  15
Asn Leu Leu Asp His Leu Glu Glu Lys Met Pro Leu Glu Asp Glu Val
            20                  25                  30
Val Pro Pro Gln Val Leu Ser Glu Pro Asn Glu Glu Ala Gly Ala Ala
        35                  40                  45
Leu Ser Pro Leu Pro Glu Val Pro Pro Trp Thr Gly Glu Val Ser Pro
    50                  55                  60
Ala Gln Arg Asp Gly Gly Ala Leu Gly Arg Gly Pro Trp Asp Ser Ser
65                  70                  75                  80
Asp Arg Ser Ala Leu Leu Lys Ser Lys Leu Arg Ala Leu Leu Thr Ala
                85                  90                  95
Pro Arg Ser Leu Arg Arg Ser Ser Cys Phe Gly Gly Arg Met Asp Arg
            100                 105                 110
Ile Gly Ala Gln Ser Gly Leu Gly Cys Asn Ser Phe Arg Tyr
        115                 120                 125
```

<210> SEQ ID NO 2
<211> LENGTH: 28
<212> TYPE: PRT
<213> ORGANISM: Homo sapiens

<400> SEQUENCE: 2

```
Ser Leu Arg Arg Ser Ser Cys Phe Gly Gly Arg Met Asp Arg Ile Gly
1               5                   10                  15
Ala Gln Ser Gly Leu Gly Cys Asn Ser Phe Arg Tyr
            20                  25
```

<210> SEQ ID NO 3
<211> LENGTH: 98
<212> TYPE: PRT
<213> ORGANISM: Homo sapiens

<400> SEQUENCE: 3

```
Asn Pro Met Tyr Asn Ala Val Ser Asn Ala Asp Leu Met Asp Phe Lys
1               5                   10                  15
Asn Leu Leu Asp His Leu Glu Glu Lys Met Pro Leu Glu Asp Glu Val
            20                  25                  30
```

```
Val Pro Pro Gln Val Leu Ser Glu Pro Asn Glu Glu Ala Gly Ala Ala
        35                  40                  45
Leu Ser Pro Leu Pro Glu Val Pro Trp Thr Gly Glu Val Ser Pro
 50                  55                  60
Ala Gln Arg Asp Gly Gly Ala Leu Gly Arg Gly Pro Trp Asp Ser Ser
 65                  70                  75                  80
Asp Arg Ser Ala Leu Leu Lys Ser Lys Leu Arg Ala Leu Leu Thr Ala
                 85                  90                  95
Pro Arg

<210> SEQ ID NO 4
<211> LENGTH: 38
<212> TYPE: PRT
<213> ORGANISM: Homo sapiens

<400> SEQUENCE: 4

Pro Glu Val Pro Pro Trp Thr Gly Glu Val Ser Pro Ala Gln Arg Asp
 1               5                  10                  15
Gly Gly Ala Leu Gly Arg Gly Pro Trp Asp Ser Ser Asp Arg Ser Ala
                20                  25                  30
Leu Leu Lys Ser Lys Leu
            35

<210> SEQ ID NO 5
<211> LENGTH: 108
<212> TYPE: PRT
<213> ORGANISM: Homo sapiens

<400> SEQUENCE: 5

His Pro Leu Gly Ser Pro Gly Ser Ala Ser Asp Leu Glu Thr Ser Gly
 1               5                  10                  15
Leu Gln Glu Gln Arg Asn His Leu Gln Gly Lys Leu Ser Glu Leu Gln
                20                  25                  30
Val Glu Gln Thr Ser Leu Glu Pro Leu Gln Glu Ser Pro Arg Pro Thr
            35                  40                  45
Gly Val Trp Lys Ser Arg Glu Val Ala Thr Glu Gly Ile Arg Gly His
     50                  55                  60
Arg Lys Met Val Leu Tyr Thr Leu Arg Ala Pro Arg Ser Pro Lys Met
 65                  70                  75                  80
Val Gln Gly Ser Gly Cys Phe Gly Arg Lys Met Asp Arg Ile Ser Ser
                 85                  90                  95
Ser Ser Gly Leu Gly Cys Lys Val Leu Arg Arg His
            100                 105

<210> SEQ ID NO 6
<211> LENGTH: 32
<212> TYPE: PRT
<213> ORGANISM: Homo sapiens

<400> SEQUENCE: 6

Ser Pro Lys Met Val Gln Gly Ser Gly Cys Phe Gly Arg Lys Met Asp
 1               5                  10                  15
Arg Ile Ser Ser Ser Ser Gly Leu Gly Cys Lys Val Leu Arg Arg His
                20                  25                  30

<210> SEQ ID NO 7
<211> LENGTH: 76
<212> TYPE: PRT
```

-continued

```
<213> ORGANISM: Homo sapiens

<400> SEQUENCE: 7

His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
        35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg
65                  70                  75
```